United States Patent
Tamura

(10) Patent No.: US 10,901,098 B2
(45) Date of Patent: Jan. 26, 2021

(54) RADIATION IMAGING SYSTEM, CONTROL APPARATUS, AND METHOD OF CONTROLLING THE SAME

(71) Applicant: CANON KABUSHIKI KAISHA, Tokyo (JP)

(72) Inventor: Toshikazu Tamura, Utsunomiya (JP)

(73) Assignee: CANON KABUSHIKI KAISHA, Tokyo (JP)

(*) Notice: Subject to any disclaimer, the term of this patent is extended or adjusted under 35 U.S.C. 154(b) by 132 days.

(21) Appl. No.: 16/361,478

(22) Filed: Mar. 22, 2019

(65) Prior Publication Data
US 2019/0302278 A1     Oct. 3, 2019

(30) Foreign Application Priority Data

Mar. 27, 2018 (JP) .................. 2018-060731

(51) Int. Cl.
| | |
|---|---|
| *G01T 1/17* | (2006.01) |
| *A61B 6/00* | (2006.01) |
| *A61B 6/02* | (2006.01) |
| *H04N 5/361* | (2011.01) |

(52) U.S. Cl.
CPC ............... *G01T 1/17* (2013.01); *A61B 6/025* (2013.01); *A61B 6/4266* (2013.01); *A61B 6/4488* (2013.01); *A61B 6/487* (2013.01); *A61B 6/505* (2013.01); *H04N 5/361* (2013.01)

(58) Field of Classification Search
CPC ...... H04N 5/361; A61B 6/542; A61B 6/5458; A61B 6/54; A61B 6/4488; A61B 8/546
See application file for complete search history.

(56) References Cited

U.S. PATENT DOCUMENTS

| | | | |
|---|---|---|---|
| 7,127,028 B2 | 10/2006 | Sendai | |
| 2010/0040199 A1* | 2/2010 | Enomoto | ............... G06T 5/008 378/98.12 |
| 2011/0317054 A1 | 12/2011 | Kameshima et al. | |
| 2016/0358330 A1* | 12/2016 | Asai | .................. A61B 6/4225 |
| 2016/0370304 A1* | 12/2016 | Asai | .................. G01N 23/04 |
| 2018/0275075 A1 | 9/2018 | Tamura et al. | |
| 2018/0292545 A1 | 10/2018 | Asai et al. | |
| 2019/0045612 A1 | 2/2019 | Tamura | |

FOREIGN PATENT DOCUMENTS

| | | |
|---|---|---|
| JP | 4510564 | 7/2010 |
| JP | 2014-168602 | 9/2014 |
| JP | 6165809 | 7/2017 |

\* cited by examiner

*Primary Examiner* — Yara B Green
(74) *Attorney, Agent, or Firm* — Venable LLP

(57) ABSTRACT

A radiation imaging system includes an imaging apparatus, an obtainment unit configured to obtain a usage mode of the imaging apparatus, a control unit configured to control the imaging apparatus to generate a radiation image and offset data, and an image processing unit configured to correct the radiation image by using the offset data. The control unit determines, based on a capability to suppress a temporal change of offset data according to the usage mode, whether to cause the imaging apparatus to generate the offset data between a start of imaging preparation and a start of radiation emission.

10 Claims, 5 Drawing Sheets

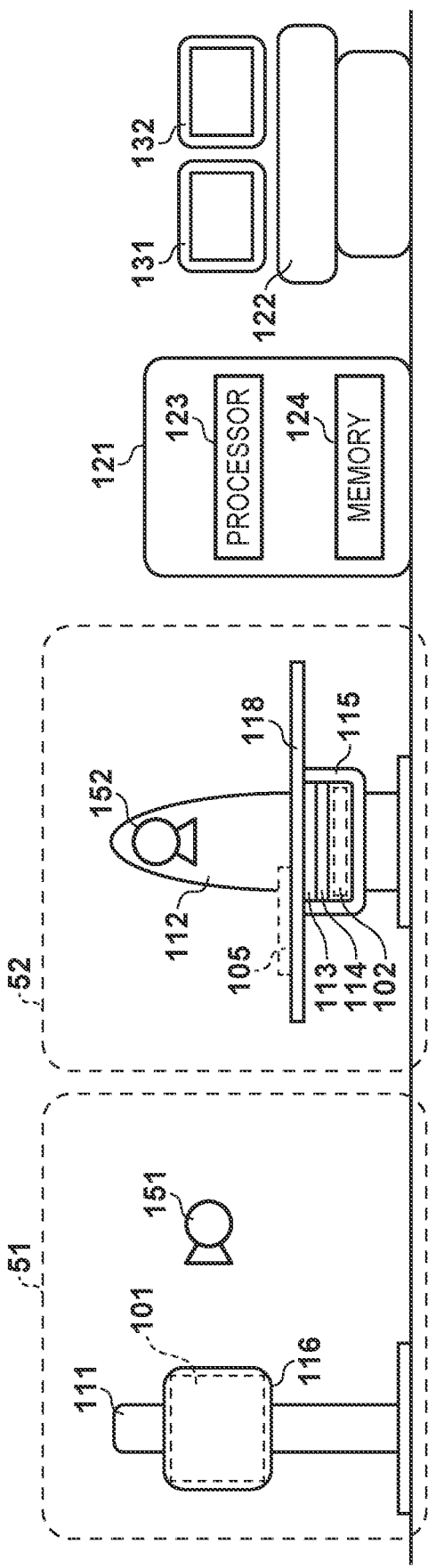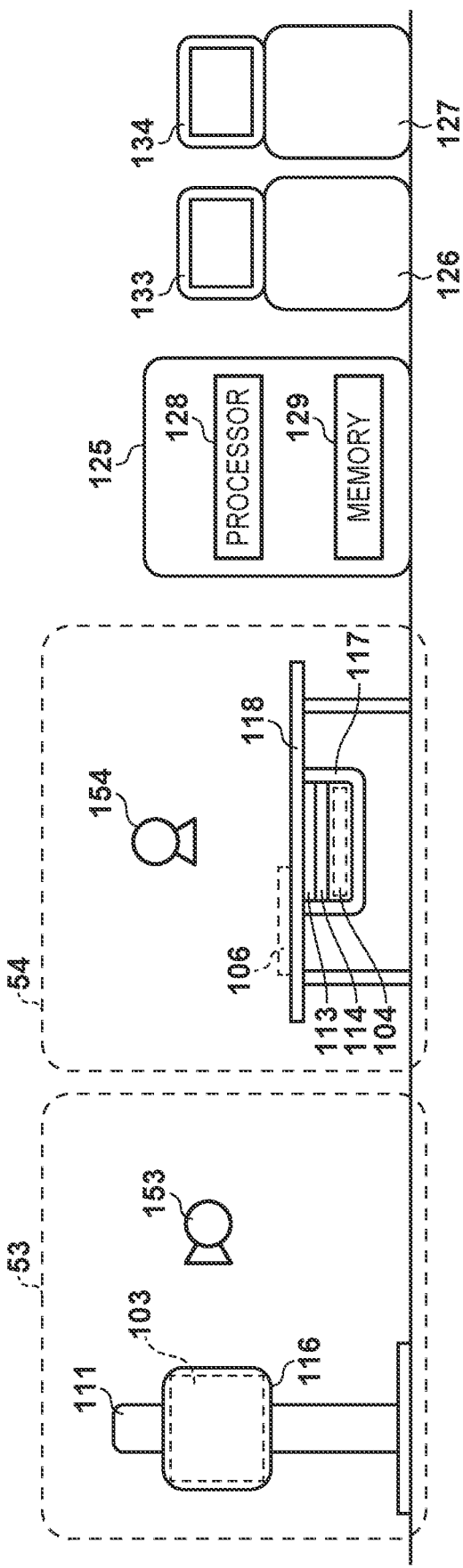

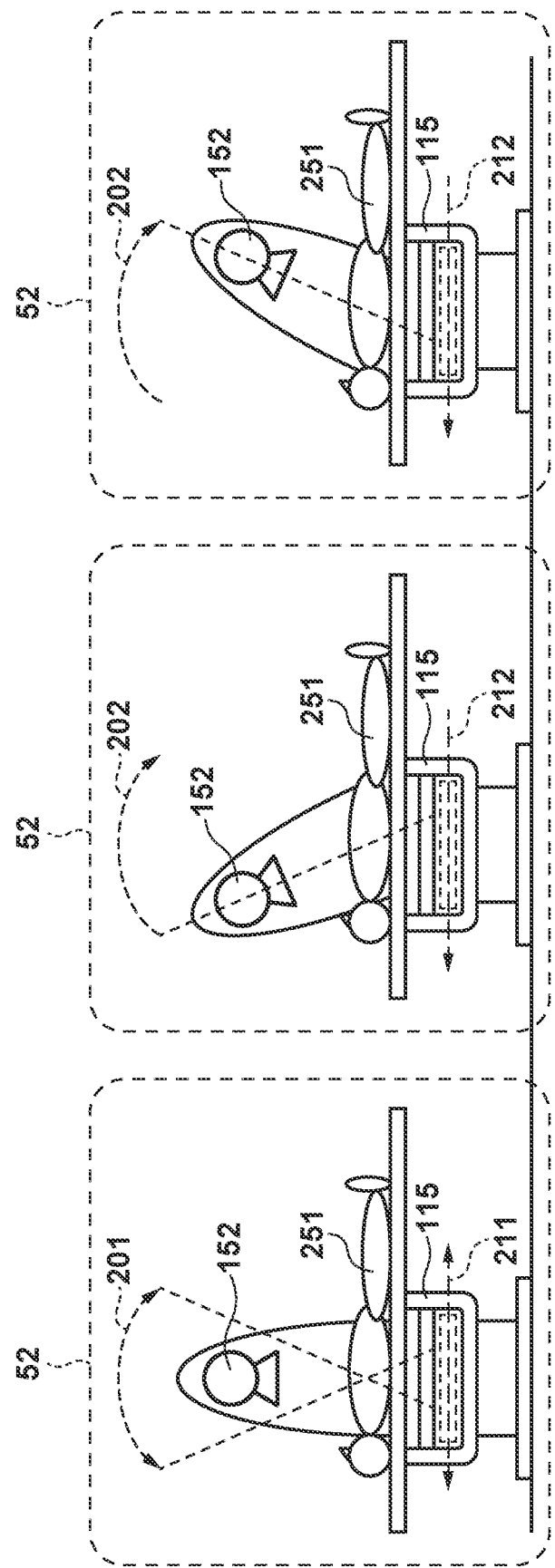

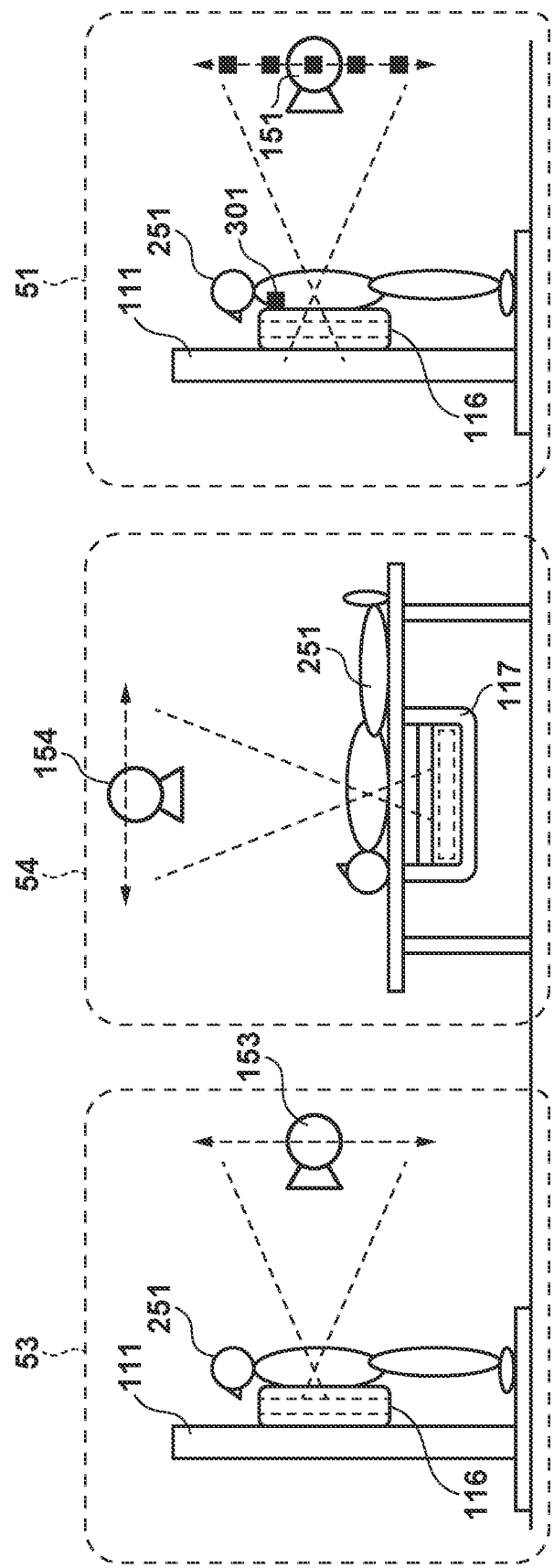

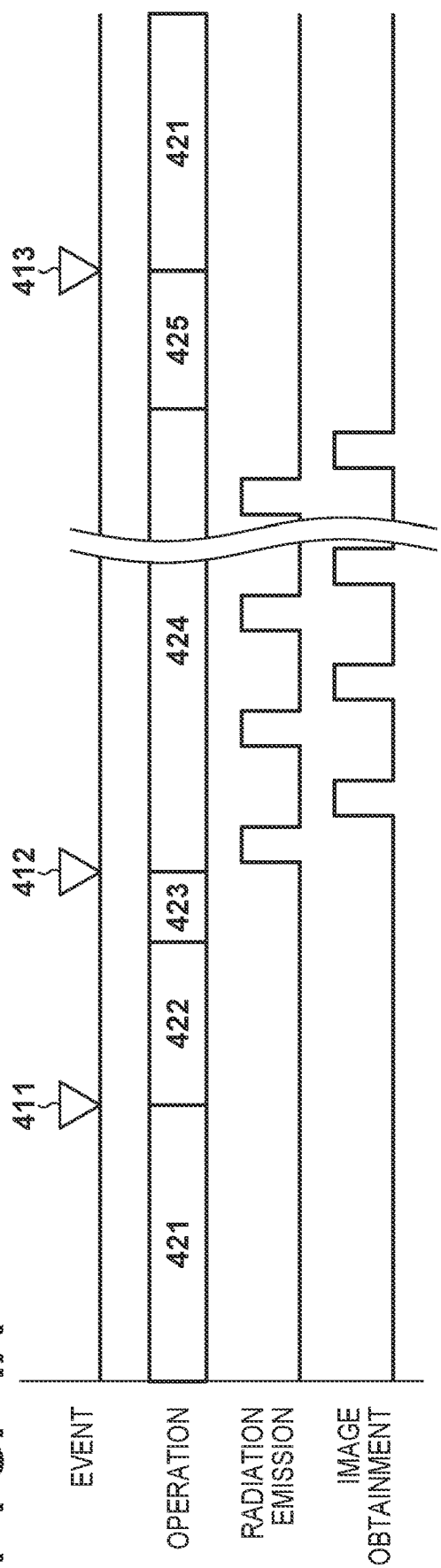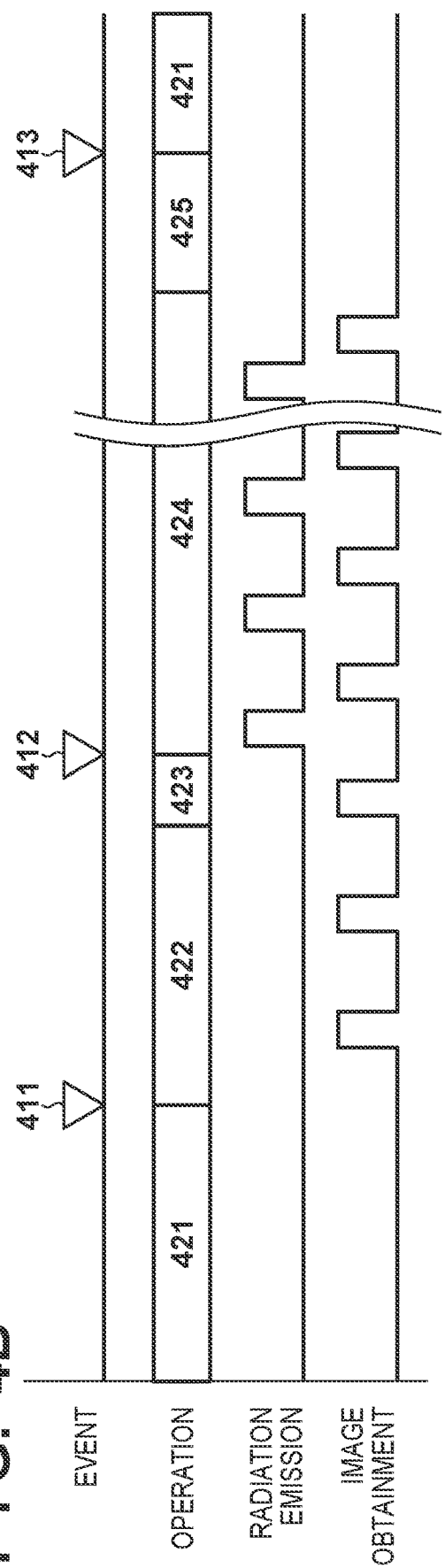

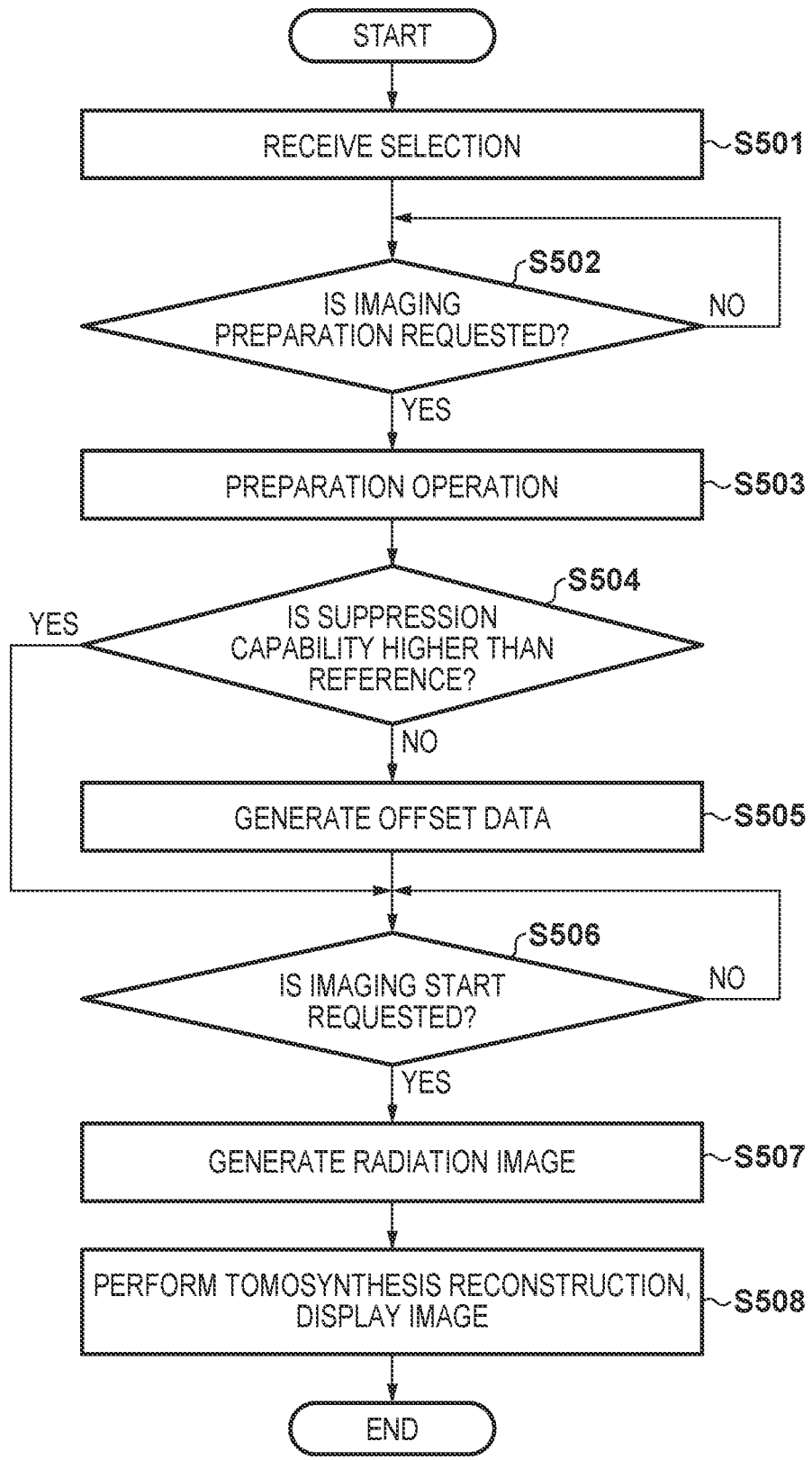

RADIATION IMAGING SYSTEM, CONTROL APPARATUS, AND METHOD OF CONTROLLING THE SAME

BACKGROUND OF THE INVENTION

Field of the Invention

The present invention relates to a radiation imaging system, a control apparatus, and a method of controlling of same.

Description of the Related Art

In recent years, systems that perform fluoroscopy or continuous imaging by using a FPD (Flat Panel Detector) of a film cassette shape for radiation imaging are being provided. Such systems can also be used in various applications such as tomosynthesis imaging, bone mineral quantity imaging, energy subtraction imaging, and stereo imaging. Some imaging apparatuses include a mechanism for stabilizing image quality (a mechanism for performing FPD temperature stabilization or imaging linking correction, for example) in order to perform the applications. Meanwhile, there also are cases in which the applications are performed by using an FPD that is mounted on a simple platform or that is positioned freely. Because such an imaging apparatus does not include a mechanism for stabilizing image quality, processes for stabilizing image quality are separately performed. In Japanese Patent Laid-Open No. 2014-168602, performing offset correction by using an FPD correction image obtained immediately prior to radiation emission is described. In Japanese Patent No. 6165809 and Japanese Patent No. 4510564, techniques for detecting misalignment of a two-dimensional image at a time of performing tomosynthesis imaging and reconstructing a radiation image after correcting the misalignment are recited.

SUMMARY OF THE INVENTION

A radiation imaging system may include a plurality of imaging apparatuses that have different capabilities such as an imaging apparatus dedicated to tomosynthesis imaging and an imaging apparatus having a simple platform. When all of the imaging apparatuses are controlled in the same way, image quality degrades in some imaging apparatuses and it takes a long time before imaging starts. An aspect of the present invention provides a technique for performing control in accordance with capabilities depending on a usage mode of an imaging apparatus.

An embodiment of the present invention provides a radiation imaging system comprising: an imaging apparatus; an obtainment unit configured to obtain a usage mode of the imaging apparatus; a control unit configured to control the imaging apparatus to generate a radiation image and offset data; and an image processing unit configured to correct the radiation image by using the offset data, wherein the control unit determines, based on a capability to suppress a temporal change of offset data according to the usage mode, whether to cause the imaging apparatus to generate the offset data between a start of imaging preparation and a start of radiation emission.

Further features of the present invention will become apparent from the following description of exemplary embodiments (with reference to the attached drawings).

BRIEF DESCRIPTION OF THE DRAWINGS

FIGS. 1A and 1B are views illustrating configuration examples of a radiation imaging system of embodiments according to the present invention.

FIGS. 2A through 2C are views illustrating operations of a radiation television fluoroscopy apparatus of embodiments according to the present invention.

FIGS. 3A through 3C are views illustrating operation of a simple platform apparatus of embodiments according to the present invention.

FIGS. 4A and 4B are timing charts of a time when tomosynthesis imaging is performed of embodiments of the present invention.

FIG. 5 is a flowchart of a time of performing tomosynthesis imaging of the embodiment of the present invention.

DESCRIPTION OF THE EMBODIMENTS

Below, description is given in detail for embodiments of the present invention with reference to the accompanying drawings. The same reference numerals are given to similar elements throughout the various embodiments so duplicate descriptions are omitted. In addition, it is possible to appropriately change and combine each embodiment. In the embodiment below, radiation may be X-rays, alpha rays, beta rays, and gamma rays.

A configuration example of a radiation imaging system is described with reference to FIGS. 1A and 1B. The radiation imaging system illustrated in FIG. 1A is equipped with a general imaging standing position apparatus 51, a radiation television fluoroscopy apparatus 52, a control unit 121, an operation console 122, and displays 131 and 132. The radiation imaging system illustrated in FIG. 1B is equipped with a general imaging standing position apparatus 53, a general imaging lying position table apparatus 54, a control unit 125, an operation console 126, a work station 127, and displays 133 and 134. The general imaging standing position apparatus 51, the radiation television fluoroscopy apparatus 52, the general imaging standing position apparatus 53, and the general imaging lying position table apparatus 54 all are imaging apparatuses for obtaining a radiation image. The plurality of imaging apparatuses coexist in one radiation imaging room and are used differently in accordance to their purpose. Each imaging apparatus performs continuous imaging which includes at least one of tomosynthesis imaging, bone mineral quantity imaging, energy subtraction imaging, and/or stereo imaging. Description is given hereinafter regarding a case in which tomosynthesis imaging is performed.

Firstly, description is given regarding the radiation imaging system of FIG. 1A. The general imaging standing position apparatus 51 is an imaging apparatus for performing standing position imaging. The general imaging standing position apparatus 51 has a standing position platform 111 and a radiation generation unit 151. The radiation generation unit 151 generates radiation for radiation fluoroscopy and imaging. A cassette holder 116 is attached to the standing position platform 111. An FPD 101 is detachable from the cassette holder 116. The cassette holder 116 holds an attached FPD 101. The FPD 101 is one example of an imaging panel that generates a radiation image by detecting radiation. A plurality of detecting elements (pixels) are arranged in an array on the detection surface of the FPD 101. The FPD 101 accumulates a signal charge generated in accordance with the amount of detected radiation in each pixel and after this obtains a signal in accordance with the signal charge as digital data by A/D conversion. Another FPD described hereinafter also has a similar configuration to the FPD 101.

The cassette holder 116 may have a connector for supplying power and communicating image signals to the FPD 101. This connector may be a contact type or a non-contact type. The standing position platform 111 does not have a mechanism (described later) for stabilizing characteristics of the FPD 101. Also, the radiation generation unit 151 does not have a function for performing alignment automatically. For this reason, an operator (a doctor or radiographer, for example) performs alignment manually. The general imaging standing position apparatus 51 can perform tomosynthesis imaging by independently performing imaging multiple times by using a phantom for alignment and the like.

The radiation television fluoroscopy apparatus 52 is an imaging apparatus for performing lying position imaging. The radiation television fluoroscopy apparatus 52 has a bed apparatus 112 for performing alignment of a subject (not shown). The bed apparatus 112 has a radiation generation portion 152, a holding portion 115, and a lying position table 118. The radiation generation portion 152 generates radiation for radiation fluoroscopy and imaging. The lying position table 118 supports the subject. The holding portion 115 is positioned under the lying position table 118. The holding portion 115 holds, in order from closest to the radiation generation portion 152, a grid 113, a radiation monitoring apparatus 114, and an FPD 102. The grid 113 removes scattered rays of radiation. The radiation monitoring apparatus 114 is used to monitor the amount of radiation to perform imaging at an appropriate radiation amount. The grid 113, the radiation monitoring apparatus 114, and the FPD 102 are all detachable from the holding portion 115. In a case where the FPD 102 has a function for monitoring the amount of radiation, configuration may be such that the radiation television fluoroscopy apparatus 52 does not have the radiation monitoring apparatus 114.

The holding portion 115 has a mechanism for performing stabilization (hereinafter referred to as a stabilization mechanism) of the characteristics of the FPD 102. The stabilization mechanism includes a mechanism for adjusting the temperature of the FPD 102. Examples of the stabilization mechanism are given below.

A mechanism for, as a thermoelectric path, causing the FPD 102 to contact a structure having a heat capacity sufficiently larger than that of the FPD 102, A mechanism for equalizing the temperature of the FPD 102 to room temperature by air-cooling the FPD 102, and A mechanism for maintaining, like a thermostat, the temperature of the FPD 102 within a predetermined temperature range based on temperature data from the FPD 102 or a measurement value for outside of the FPD 102.

The radiation television fluoroscopy apparatus 52 is capable of imaging limbs and the like by combining an FPD 105 placed on a table top with the radiation generation portion 152 or the radiation generation unit 151. In this apparatus, tomosynthesis imaging can be quickly executed with good positional accuracy between the radiation generation portion 152 and the FPD 102.

The control unit 121 performs control of the whole radiation imaging system such as control of radiation generation, FPD synchronization control, image obtainment, and image processing. The control unit 121 has a processor 123 and a memory 124. Operation of the control unit 121 may be executed by the processor 123 executing a program read into the memory 124. Furthermore, the control unit 121 may have a dedicated circuit (an ASIC (application specific integrated circuit), for example) for executing some or all of operations of the control unit 121. The control unit 121 may be called a control apparatus. The control apparatus may include an obtainment unit, a control unit, and an image processing unit. The control unit 121 may be a stand-alone apparatus as illustrated in FIG. 1A and may be distributed to a plurality of apparatuses. Also, some of the functions of the control unit 121 may be executed by the imaging apparatus.

The operation console 122 accepts settings for the radiation generation unit or settings for an image obtainment mode from the operator. When positioning of the subject is complete, the operator performs fluoroscopy or imaging by a radiation emission start button or a foot switch on the operation console 122. In accordance with this, radiation images based on the settings are displayed on the displays 131 and 132. An image for fluoroscopy is displayed on the display 131 and an image for reference is displayed on the display 132.

Continuing on, description is given regarding the radiation imaging system of FIG. 1B. The general imaging standing position apparatus 53 is an imaging apparatus for performing standing position imaging. The general imaging standing position apparatus 53 has a standing position platform 111 and a radiation generation unit 153. The radiation generation unit 153 generates radiation for radiation fluoroscopy and imaging. A cassette holder 116 is attached to the standing position platform 111. An FPD 103 is detachable from the cassette holder 116. The radiation generation portion 153 has a function for automatically operating in order to perform tomosynthesis imaging.

The general imaging lying position table apparatus 54 is an imaging apparatus for performing lying position imaging. The general imaging lying position table apparatus 54 has a holding portion 117, the lying position table 118, and a radiation generation portion 154. The radiation generation portion 154 generates radiation for radiation fluoroscopy and imaging. The radiation generation portion 154 has a function for automatically operating in order to perform tomosynthesis imaging. The holding portion 117 is positioned under the lying position table 118. The holding portion 117 holds, in order from closest to the radiation generation portion 154, a grid 113, a radiation monitoring apparatus 114, and an FPD 104. Unlike the previously described radiation television fluoroscopy apparatus 52, the holding portion 117 does not have the above described stabilization function. A single-bodied radiation generation portion may be used as the radiation generation portions 153 and 154.

The control unit 125 performs control of the whole radiation imaging system similarly to the control unit 121. The control unit 125 has a processor 128 and a memory 129 similarly to the control unit 121. The operation console 126 accepts settings for the radiation generation unit or settings for an image obtainment mode from the operator. When positioning of the subject is complete, the operator performs fluoroscopy or imaging by a radiation emission start button or a foot switch on the operation console 126. In accordance with this, radiation images based on the settings are displayed on the display 133. The work station 127 obtains from the control unit 125 an image of values proportional to the radiation amounts or obtains an image that can be converted into values proportional thereto, performs reconstruction on the image, and displays the result on the display 134.

In the description above, the radiation imaging system of FIG. 1A has the general imaging standing position apparatus 51 and the radiation television fluoroscopy apparatus 52, and the radiation imaging system of FIG. 1B has the general imaging standing position apparatus 53 and the general imaging lying position table apparatus 54. Combinations of imaging apparatuses that the systems have are not limited to this, and there may be any combination having a plurality of imaging apparatus.

Continuing on, description is given regarding processing for correcting the radiation image obtained from the FPD 101. Processing of the radiation image obtained from another FPD and processing of the control unit 125 are similar. An image (hereinafter referred to as a radiation image) in accordance with the charges accumulated in the pixels after radiation was emitted onto the FPD 101 includes an offset component error and a gain component error. The offset component error is an error caused by charge accumulated in pixels in a state in which radiation is not emitted (a so-called dark charge). The gain component error is an error caused by sensitivity of the pixels within the FPD and the analog IC. The control unit 121 corrects these errors. Data for correcting the gain component error (hereinafter referred to as gain data) is generated by obtaining, in the factory or upon installation in a hospital, a radiation image in a state where there is no subject, and then normalizing the reciprocal of each pixel value. Gain data can be held in the memory 124 of the control unit 121. It is possible to sufficiently suppress the influence on image quality if gain data is updated at a time of regular maintenance or the like because there is only moderate temporal change in the gain component error.

Data for correcting the offset component error (hereinafter referred to as offset data) can be obtained by the FPD executing a similar operation to the imaging operation in a state in which radiation is not emitted. In this way, the offset data can also be referred to as dark correction data because it is obtained without emission of radiation corresponding to a flash. Due to a temperature change due to heat generation within the FPD, the usage order of specific operation modes, or the like, the offset component error may change in a short amount of time to the extent that it imparts an observable effect on the radiation image. For this reason, it is possible to improve the image quality of the radiation image by updating the offset data such that a change of the offset component error is contained within a tolerable range. Furthermore, it is possible to reduce noise of random components included in the offset data by generating offset data multiple times and taking an average of the data.

It is possible to reduce the difference between the offset component error included in a radiation image and the offset data used in the generation of the radiation image by correcting the radiation image by using offset data generated immediately prior to the start of the radiation emission. Immediately prior to the start of the radiation emission means the period from the start of imaging preparation to the start of the radiation emission, for example. However, in that case, is it not possible to start imaging until generation of the offset data has finished. In the present embodiment, in a case where the radiation image is generated by using the stabilization mechanism of the imaging apparatus, offset data is not generated immediately prior to the start of radiation emission. Due to the stabilization mechanism, image quality of the radiation image is maintained even if offset data generated prior to the start of the imaging preparation is used because temporal change in the offset data is suppressed. Meanwhile, in a case where the radiation image is generated without using the stabilization mechanism of the imaging apparatus, offset data is generated immediately prior to the start of radiation emission. As a result, it is possible to suppress degradation of the image quality due to the temporal change of the offset data.

Continuing on, with reference to FIG. 2A-C and FIG. 4A, an operation example in which the control unit 121 performs tomosynthesis imaging by using the radiation television fluoroscopy apparatus 52 is described. As described above, the radiation television fluoroscopy apparatus 52 has a stabilization mechanism. For this reason, the control unit 121 does not generate offset data in the period from the start of imaging preparation to the start of the radiation emission. FIG. 2A illustrates a state in which the position of the radiation television fluoroscopy apparatus 52 is at an initial position. The radiation generation portion 152 is at a position where normal fluoroscopy and imaging are performed. The radiation generation portion 152 can move in the range of an arrow 201. The holding portion 115 can move in the range of an arrow 211.

In FIGS. 4A and 4B, "event" indicates an event with respect to the operator. "Operation" indicates an operation of the radiation imaging system. "Radiation emission" indicates a state of emission of radiation. The low level indicates that radiation is not being emitted and the high level indicates that radiation is being emitted. "Image obtainment" indicates a state of image obtainment from the FPD. The low level indicates that an image is not being obtained and the high level indicates that an image is being obtained.

When an operation starts (after activation of the FPD, for example), the radiation imaging system enters a standby state 421. The operator performs an imaging preparation request 411 for tomosynthesis imaging from the operation console 122 or the like when positioning of the subject 251 is finished. In accordance with the imaging preparation request 411, the radiation imaging system performs an imaging preparation operation 422. Specifically, the control unit 121 moves the radiation generation portion 152 and the holding portion 115 to a position indicated in FIG. 2B. When movement is finished, the radiation imaging system enters an imaging ready state 423.

The operator performs an imaging start request 412 after the radiation imaging system enters the imaging ready state 423. In accordance with the imaging start request 412, the radiation imaging system performs an imaging operation 424. Specifically, the radiation imaging system moves the radiation generation portion 152 in the direction of an arrow 202 and moves the holding portion 115 in the direction of an arrow 212 while repeating emission of radiation. As a result, the radiation generation portion 152 and the holding portion 115 move to the position indicated in FIG. 2C. The FPD 102 performs generation of a radiation image synchronized with the radiation emission and transmits the obtained radiation images to the control unit 121 in turn. The control unit 121 performs offset correction and gain correction on the radiation images. The offset data generated prior to the start of the imaging preparation is used for the offset correction. The number of imaged radiation images is approximately 32 to 128, for example, and imaging is performed per one sheet by a radiation amount such that the amount of emitted radiation on the subject does not become too large with respect to the radiation amount of plain imaging.

The radiation imaging system performs an image reconstruction operation 425 after the scheduled number of radiation images has been obtained. After this, the radiation imaging system performs an image display 413 for displaying the image obtained by reconstruction to the operator and then returns to the standby state 421.

Continuing on, with reference to FIGS. 3A through 3C and FIG. 4B, description is given regarding an operation example in which tomosynthesis imaging is performed by the control unit 121 using the general imaging standing position apparatus 51 or by the control unit 125 using the general imaging standing position apparatus 53 or the general imaging lying position table apparatus 54. As described above, the general imaging standing position apparatus 51, the general imaging standing position apparatus 53, and the general imaging lying position table apparatus 54 do not have a stabilization mechanism. For this reason, the control unit 121 generates offset data in the period from the start of imaging preparation to the start of the radiation emission.

When an operation starts (after activation of the FPD, for example), the radiation imaging system is in the standby state 421. The operator performs the imaging preparation request 411 from the operation console 122 or the like when positioning of the subject 251 is finished. In accordance with the imaging preparation request 411, the radiation imaging system performs the imaging preparation operation 422. Specifically, the radiation imaging system generates offset data.

Operations of the radiation generation portions 153 and 154 in the general imaging standing position apparatus 53 and the general imaging lying position table apparatus 54 are similar to the operations of the radiation generation portion 152 of the radiation television fluoroscopy apparatus 52. While the radiation generation portion 152 moves in an arc, the radiation generation portions 153 and 154 are different in that they move in a line. Also, the FPD does not move in the general imaging standing position apparatus 53 and the general imaging lying position table apparatus 54. Because there exist cases such as where the position of the radiation generation portion 153 or 154 is largely separated from the imaging position for tomosynthesis imaging, the imaging preparation operation 422 takes more time than in a case where the radiation television fluoroscopy apparatus 52 is used.

One example of the general imaging standing position apparatus 51 is illustrated in FIG. 3C. The radiation imaging system images a positioning phantom 301 together with the subject 251 because the general imaging standing position apparatus 51 does not have a mechanism for automatically operating the radiation generation unit 151. Also, the operator performs radiation imaging one image at a time. Since the number of radiation images obtained in this method is low, it is possible to set the amount of radiation to a larger amount per image. The radiation imaging system may obtain one image worth of offset data immediately after generation of each radiation image.

The control unit 121 may generate offset data multiple times and average these data in order to suppress a random noise component. Generation of the offset data multiple times may be executed immediately after the start of the imaging preparation operation 422. Also, generation of the offset data multiple times may be executed immediately before the imaging start request 412. By repeating generation of the offset data until immediately prior to the imaging start request 412, the offset data can be generated in a state that is close to that when the radiation images are obtained.

In order to average the offset data, the control unit 121 may have a plurality of frame memories, sequentially update the frame memories as with a FIFO memory, and immediately calculate the offset data in hardware processing after the imaging start request 412 is received. Also, the control unit 121 may perform averaging by successively adding the offset data. Additionally, the control unit 121 may perform offset correction and the like after calculation of the offset data is completed by saving the radiation images in the frame memory. Since the operations from the imaging start request 412 are similar to when the radiation television fluoroscopy apparatus 52 is used, description is omitted.

With reference to FIG. 5, description is given regarding an operation example of the control unit 121. The control unit 125 performs similar operations. The processing of FIG. 5 is started by the radiation imaging system being activated, for example. After activation, the radiation imaging system may enter the standby state 421. In the standby state 421, the control unit 121 causes generation of the offset data for each of the plurality of imaging apparatuses. The generated offset data is stored in the memory 124, for example.

In step S501, the control unit 121 obtains a selection of an imaging apparatus from the operator and a usage mode of the imaging apparatus. The operator selects one of the plurality of imaging apparatuses included in the radiation imaging system and designates the usage mode of the imaging apparatus. For example, in a case where the operator selects an imaging apparatus having a stabilization mechanism such as the radiation television fluoroscopy apparatus 52, the operator designates whether or not the stabilization mechanism will be used. Meanwhile, in a case where the operator selects an imaging apparatus not having a stabilization mechanism, the operator cannot designate that the stabilization mechanism will be used.

In step S502, the control unit 121 determines whether or not the imaging preparation request 411 is received from the operator. In a case where the request is received (YES in step S502), the control unit 121 advances the processing to step S503, and in a case where the request is not received (NO in step S502), the control unit 121 repeats step S502. The control unit 121 executes the above described imaging preparation operation 422 in step S503.

In step S504, the control unit 121 determines whether or not a capability to suppress (hereinafter referred to as suppression capability) the temporal change of offset data according to the usage mode of the selected imaging apparatus is higher than a reference. In a case where the suppression capability is higher than the reference (YES in step S504), the control unit 121 advances the processing to step S506, and in a case where the suppression capability is lower than the reference (NO in step S504), the control unit 121 advances the processing to step S505. In a case where the suppression capability is the same as the reference, the control unit 121 may advance the processing to either step. The control unit 121 may determine that the suppression capability is higher than the reference in a case where the above described stabilization mechanism is used, for example, and may determine that the suppression capability is lower than the reference in a case where the stabilization mechanism is not used.

In step S505, the control unit 121 causes the selected imaging apparatus to generate the offset data. The control unit 121 may cause the offset data to be generated by excluding a window in which an afterimage greatly remains in the FPD image, a window in which image quality has not been stabilized immediately after a driving mode is changed, and a window in which it is predicted that artifacts will be produced due to a large acceleration/shock on the FPD, or the like. The generation of the offset data may be ended after a predetermined number of generations and may be performed until immediately prior to the imaging start request 412.

In step S506, the control unit 121 determines whether or not the imaging start request 412 is received from the operator. In a case where the request is received (YES in step S506), the control unit 121 advances the processing to step S507, and in a case where the request is not received (NO in step S506), the control unit 121 repeats step S506. The control unit 121 executes the above described imaging operation 424 in step S507. The control unit 121 repeatedly generates radiation images in this operation. Furthermore, the radiation images can be corrected by using the offset data and gain data. In step S508, the control unit 121 performs a tomosynthesis reconstruction and displays an obtained tomosynthesis image on the display.

In the above described method, the control unit 121 determines whether or not the selected imaging apparatus is caused to generate the offset data between the start of imaging preparation and the start of radiation emission, based on the suppression capability according to the usage mode of the selected imaging apparatus. Specifically, the control unit 121 determines whether or not to cause the selected imaging apparatus to generate the offset data between the start of imaging preparation and the start of radiation emission, based on the suppression capability according to the usage mode of the selected imaging apparatus being less than a reference. As a result, image quality of the radiation image after correction improves. Meanwhile, in a case where the suppression capability of the usage mode of the selected imaging apparatus is higher than the reference, the control unit 121 does not cause the selected imaging apparatus to generate the offset data between the start of imaging preparation and the start of radiation emission. By this, the time until the start of imaging is shortened. The control unit 121 causes the selected imaging apparatus to generate the offset data prior to the start of imaging preparation in a case where the suppression capability of the usage mode of the selected imaging apparatus is higher than the reference. Correction of the radiation image is performed by using this offset data.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2018-060731, filed Mar. 27, 2018, which is hereby incorporated by reference herein in its entirety.

What is claimed is:

1. A radiation imaging system comprising:
    an imaging apparatus;
    an obtainment unit configured to obtain a usage mode of the imaging apparatus;
    a control unit configured to control the imaging apparatus to generate a radiation image and offset data; and
    an image processing unit configured to correct the radiation image by using the offset data, wherein
    the control unit determines, based on a capability to suppress a temporal change of offset data according to the usage mode, whether to cause the imaging apparatus to generate the offset data between a start of imaging preparation and a start of radiation emission.

2. The system according to claim 1, wherein the control unit
    causes the imaging apparatus to generate the offset data between the start of imaging preparation and the start of radiation emission in a case where the capability to suppress according to the usage mode is lower than a reference, and
    does not cause the imaging apparatus to generate the offset data between the start of imaging preparation and the start of radiation emission in a case where the capability to suppress according to the usage mode is higher than a reference.

3. The system according to claim 2, wherein the control unit causes the imaging apparatus to generate the offset data prior to the start of imaging preparation in a case where the capability to suppress according to the usage mode is higher than the reference.

4. The system according to claim 2, wherein the control unit determines that the capability to suppress is higher than the reference in a case where the usage mode includes using a mechanism for adjusting the temperature of an imaging panel.

5. The system according to claim 1, wherein an imaging panel is removable from the imaging apparatus.

6. The system according to claim 1, wherein the imaging apparatus repeatedly generates the radiation image.

7. The system according to claim 1, wherein the imaging apparatus performs at least one of tomosynthesis imaging, bone mineral quantity imaging, energy subtraction imaging, and/or stereo imaging.

8. The system according to claim 1, wherein the usage mode includes imaging in a standing position or imaging in a lying position.

9. A control apparatus for a radiation imaging system, the apparatus comprising:
    an obtainment unit configured to obtain a usage mode of an imaging apparatus;
    a control unit configured to control the imaging apparatus to generate a radiation image and offset data; and
    an image processing unit configured to correct the radiation image by using the offset data, wherein
    the control unit determines, based on a capability to suppress a temporal change of offset data according to the usage mode, whether to cause the imaging apparatus to generate the offset data between a start of imaging preparation and a start of radiation emission.

10. A method for controlling a radiation imaging system, the method comprising:
    obtaining a usage mode of an imaging apparatus;
    controlling the imaging apparatus to generate a radiation image and offset data; and
    correcting the radiation image by using the offset data, wherein
    based on a capability to suppress a temporal change of offset data according to the usage mode, it is determined whether to cause the imaging apparatus to generate the offset data between a start of imaging preparation and a start of radiation emission.

* * * * *